United States Patent [19]

Padron

[11] Patent Number: 5,359,038
[45] Date of Patent: * Oct. 25, 1994

[54] METHOD FOR ISOLATING IMMUNOGLOBULIN COMPOUNDS IN THE FECES

[76] Inventor: Eloy Padron, 7841 SW. 134th Ter., Miami, Fla. 33156

[*] Notice: The portion of the term of this patent subsequent to Oct. 13, 2009 has been disclaimed.

[21] Appl. No.: 50,166

[22] PCT Filed: Jul. 14, 1992

[86] PCT No.: PCT/US90/05826

§ 371 Date: May 3, 1993

§ 102(e) Date: May 3, 1993

[51] Int. Cl.$^5$ ............................................ A61K 39/395
[52] U.S. Cl. .............................. 530/390.5; 530/387.1; 530/390.1; 530/861; 530/862; 530/863
[58] Field of Search .............. 530/390.1, 390.5, 387.1, 530/861, 862, 863

[56] References Cited

U.S. PATENT DOCUMENTS 5,155,213 10/1992 Padron ........................... 530/387.1

Primary Examiner—Howard E. Schain
Attorney, Agent, or Firm—J. Sanchelima

[57] ABSTRACT

A method for isolating the immunoglobulin compounds in the feces of animals and humans including the steps of placing said feces in a container with a buffer solution, homogenizing the feces in a phosphate buffer saline solution thereby forming a homogenized solution, separating the solids from the homogenized solution leaving a clear solution and chemically precipitating substantially all material contained in the clear solution with the exception of the immunoglobulin compounds through the use of protamine. The method produces a sufficient amount of immunoglobulin compounds for diagnostic and treatment purposes, if necessary. In particular, the production of IgAs has been quite useful for these purposes.

8 Claims, No Drawings

METHOD FOR ISOLATING IMMUNOGLOBULIN COMPOUNDS IN THE FECES

TECHNICAL FIELD

The present invention relates to a method for isolating the immunoglobulin compounds, namely, IgAs, IgMs, IgD, IgG and its subclasses 1; 2; 3 and 4 in human and animal feces, and more particularly, to such method that is used in the diagnosis and treatment of allergies and diseases associated with deficiencies in the immulogical system of patients.

BACKGROUND ART

Applicant believes that the closest reference corresponds to a seminar that took place in San Francisco and sponsored by the American College of Allergy & Immulogy (47th Annual Meeting) in November of 1990 (lecturers: J. E. Postley, M. D. and J. Einbinder, PhD) wherein it was discussed that IgAs can be obtained from the saliva to make certain determinations concerning the presence of antigens/antibodies. The method disclosed, however, required the production of approximately 30 cc of saliva from a patient in order to obtain IgAs in the micro-grams range. The unreliability of using any conventional diagnosis method from these minimal quantities of IgAs is quite apparent. Also, the undesirability of the method from the patient's standpoint is obvious.

To determine the presence of antigens and/or antibodies many conventional methods have been used in the past. Most of them, using an enzyme conjugated with another chemical substance to detect the presence, and with some methods, approximate the quantity of the antigens and antibodies. Typically, these methods are used in conjunction with blood drawn from the patient and the immunoglobin classes tested are the IgE and IgG4. However, IgAs is not present in the blood drawn from an individual in appreciable quantities since it is mainly created by the mucous, such as the intestines' mucous membranes, and being eventually stored in the feces. The information carried in general immunity IgE and IgG4 is not as relevant for diagnostic purposes as the information included in the local immunity IgAs. The conventional methods include those that use conjugated enzymes, such as, ELISA, RIA, radio immuno assay, immunoofluorescent methods, dots/-disks, strips methods, etc. None of these methods are directed towards the use of IgAs since it is not present in the blood drawn from the patient in appreciable quantifies.

None of the methods presently used for detection of the presence of antigens and/or antibodies utilize IgMs because it is not found in the blood in sufficient amounts. However, when used with IgAs it provides valuable information in the diagnostis of diseases caused by bacterias, viruses and certain tumural lesion on the digestive tract.

SUMMARY OF THE INVENTION

It is one of the main objects of the present invention to provide a method for detecting, identifying qualitatively and quantitatively the presence of antigens and antibodies in a person or animal through the isolation of the immunoglobulin compounds.

It is another object of this invention to provide a method that is reliable and does not present inconveniences to the user.

It is still another object of the present invention to provide a method that can be readily used.

It is yet another object of this invention to provide such a method that is inexpensive to utilize.

It is yet another object of this present invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

DETAILED DESCRIPTION OF THE PREFERRED EMBODIMENT

The preferred manner of practicing the present invention will be described below. The inventor has obtained excellent results, compared to the other conventional methods. The key is to isolate a sufficiently large amount of the immunoglobulin compounds in order to accurately determine the presence of antigens and/or antibodies. The different immunoglobulin compounds, namely, IgAs, IgMs, IgD, IgG, $IgG_1$, $IgG_2$, $IgG_3$ and $IgG_4$, which are collectively referred to as the immunoglobulin compounds. The first step is to obtain the feces, human or animal, and place them in a container with a buffer solution. This buffer solution can be implemented with the use of a water base solution that includes a phosphate and sodium chloride, such as conventionally known PBS (phosphate buffer saline) solution. Preferably, a 0.010 molar solution is used with a pH of 7.6. In the preferred manner contemplated by the inventor, 10% of the weight will be the feces and the remaining 90% will be the buffer solution. This is not critical and in practice the buffer solution is estimated by volume and the feces by weight, equating the densities of the feces and the buffer solution. Also, merthiolate (0.1% concentration) is added to kill any bacteria and to minimize the odor of the feces.

The second step involves the homogenization of the feces in the buffer solution and this is accomplished with an homogenizer rotating its blades at 28,000 R.P.M. in the preferred embodiment. This is done for approximately 5 minutes. The resulting liquid is typically brown and the lympho cells are destroyed.

Then, the homogenizer is stopped (allowed to settle) for 5 minutes and after that it is started again for another 5 minutes. Again, it is stopped once more and started once again for the final 5 minutes. After that, the liquid is centrifuged to separate the solids from the liquid and depending on the particular constitution of the feces (fiber content, etc.) sufficient time is allowed for the liquid to clear. It has been empirically determined that three cycles of homogenzation and settlement are sufficient for the destruction of the lymphocytes cells and the freeing up of the immunoglobulin compounds contained therein.

The next step is to add protamine (at 1% concentration, a fish extract typically) so that everything precipitates except the immunoglobulin compounds which remains either in solution (conjugated with the protamine) or in suspension. In the preferred case, about 1 mg. in 1% concentration is added to about 6 or 7 cc of the clear liquid after decanting. In a typical case, the inventor herein has been able to obtain samples in the order of hundreds of milligram of the immunoglobulin compounds which are enough for accurate analysis using the conventional enzyme methods described above (ELISA, RIA, and others). The immunoglobin compounds can be detected and classified usgin conventional methods.

The production of immunoglobulin compounds in sufficient quantities makes it possible not only to properly diagnose the patients' immulogical deficiencies but also to produce these compounds in sufficiently large quantifies to administer it conjugated with the pertinent allergens to rebuild the patients' immunity.

INDUSTRIAL APPLICABILITY

It is apparent from the previous paragraphs that an improvement of the type for such a method is quite desirable for detecting, identifying qualitatively and quantitatively the presence of antigens and antibodies in a person or animal and is reliable and does not present inconveniences to the user.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method for isolating IgAs in the feces of animals and humans including the steps of:
   A. placing said feces in a container with a buffer solution;
   B. homogenizing the feces in said buffer solution thereby forming a homogenized solution;
   C. separating the solids from said homogenized solution leaving a clear solution; and
   D. chemically precipitating substantially all material contained in said clear solution with the exception of the IgAs, IgMs, IgD, IgG and its subclasses 1; 2; 3 and 4 through the use of protamine and using a conventional method for the detection and classification of antigens and antibodies found in said isolated IgAs, IgMs, IgD, IgG and its subclasses 1; 2; 3 and 4.

2. The method set forth in claim 1 wherein said step of chemically precipitating the material contained in said clear solution with the exception of said IgAs includes the use of an effective amount of protamine.

3. The method set forth in claim 2 wherein said buffer solution includes an effective amount of a bacteria suppressing substance.

4. The method set forth in claim 3 wherein said bacteria suppressing substance includes a merthiolate solution.

5. The method set forth in claim 4 wherein in said homogenized solution substantially all lymph cells have been destroyed.

6. The method set forth in claim 5 wherein said homogenizing step is performed twice and having a rest period in between.

7. The method set forth in claim 6 wherein said buffer solution includes a phosphate buffer saline solution.

8. The method set forth in claim 7 wherein said homogenization is performed with a homogenizer with blades that rotate at a speed in excess of 20,000 revolutions per minute.

* * * * *